(12) United States Patent
Mignogna et al.

(10) Patent No.: US 9,481,745 B2
(45) Date of Patent: Nov. 1, 2016

(54) CATALYST COMPONENTS FOR THE POLYMERIZATION OF OLEFINS

(71) Applicant: BASELL POLIOLEFINE ITALIA S.R.L., Milan (IT)

(72) Inventors: Alessandro Mignogna, Ferrara (IT); Reynald Chevalier, Frankfurt (DE); Giampiero Morini, Ferrara (IT); Martin Schneider, Hochheim (DE)

(73) Assignee: Basell Poliolefine Italia S.r.l., Milan (IT)

( * ) Notice: Subject to any disclaimer, the term of this patent is extended or adjusted under 35 U.S.C. 154(b) by 0 days.

(21) Appl. No.: 14/917,549

(22) PCT Filed: Sep. 8, 2014

(86) PCT No.: PCT/EP2014/069056
§ 371 (c)(1),
(2) Date: Mar. 8, 2016

(87) PCT Pub. No.: WO2015/032939
PCT Pub. Date: Mar. 12, 2015

(65) Prior Publication Data
US 2016/0208027 A1    Jul. 21, 2016

(30) Foreign Application Priority Data
Sep. 9, 2013 (EP) .................................... 13183493

(51) Int. Cl.
| | |
|---|---|
| *C08F 4/00* | (2006.01) |
| *C08F 4/52* | (2006.01) |
| *C08F 210/00* | (2006.01) |
| *C07C 205/00* | (2006.01) |
| *C08F 110/06* | (2006.01) |
| *C07C 271/12* | (2006.01) |

(52) U.S. Cl.
CPC ........... *C08F 110/06* (2013.01); *C07C 271/12* (2013.01)

(58) Field of Classification Search
CPC ....................................... C08F 110/06
USPC ............................... 526/90, 189, 348; 560/21
See application file for complete search history.

(56) References Cited

U.S. PATENT DOCUMENTS

| | | | |
|---|---|---|---|
| 4,568,382 A * | 2/1986 | Liu ........................ | A01N 37/40 504/303 |
| 2011/0130529 A1 | 6/2011 | Coalter, III et al. | |
| 2012/0316299 A1 | 12/2012 | Chen et al. | |

FOREIGN PATENT DOCUMENTS

| | | |
|---|---|---|
| EP | 2803678 A1 | 11/2014 |
| WO | WO-2006110234 A2 | 10/2006 |

* cited by examiner

*Primary Examiner* — William Cheung

(57) ABSTRACT

The present technology relates to a solid catalyst component for the polymerization of olefins comprising Mg, Ti and an electron donor of the general formula (I):

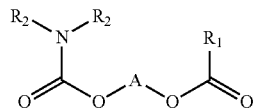

where $R_1$ is selected from $C_1$-$C_{15}$ hydrocarbon groups, the $R_2$ groups are equal to or different from each other, are hydrogen, or the $R_1$ groups can be fused together to form one or more cycles and A is a bivalent bridging group. The catalyst components of the present disclosure exhibit high activity and stereospecificity in the polymerization of olefins.

15 Claims, No Drawings

CATALYST COMPONENTS FOR THE POLYMERIZATION OF OLEFINS

This application is the U.S. National Phase of PCT International Application PCT/EP2014/069056, filed Sep. 8, 2014, claiming benefit of priority to European Patent Application No. 13183493.9, filed Sep. 9, 2013, the contents of which are incorporated herein by reference in its entirety.

FIELD OF THE INVENTION

The present disclosure relates to catalyst components for the polymerization of olefins, such as propylene, comprising a magnesium (Mg) dihalide based support on which are supported titanium (Ti) atoms and an electron donor compound containing an ester and a carbamate. The present disclosure further relates to the catalysts obtained from the reaction of these components and to their use in processes for the polymerization of olefins such as propylene.

BACKGROUND OF THE INVENTION

Catalyst components for the stereospecific polymerization of olefins are known in the art. The polymerization of olefins such as propylene is often performed using Ziegler-Natta catalysts which comprise a solid catalyst component such as a magnesium (Mg) dihalide on which a titanium (Ti) compound and an internal electron donor compound may be supported, and optionally an Al-alkyl compound. When high polymeric crystallinity is required, an external donor (for example, an alkoxysilane) may be further required to obtain higher isotacticity. In addition, internal donors such as esters of phthalic acid, including diisobutylphthalate, may be used. The phthalates are often used as internal donors in combination with alkylalkoxysilanes as external donors. This catalyst system often gives good performance in terms of activity, isotacticity and xylene insolubility.

However, one of the problems associated with the use of this catalyst system is the potential health concerns associated with the use of phthalates.

Consequently, many research activities have been devoted to the discovery of alternative classes of internal donors for use in the preparation of catalyst components for propylene polymerization.

Some of the tested catalysts contain donor structures having amido and ester groups. For instance, WO 2006/110234 describes amino acid derivatives, including one carbamate group and one free ester function, that may be used as internal donors. The catalysts generated by these structures have very low activity and sterospecificity in bulk propylene polymerization (Table 2).

SUMMARY OF THE INVENTION

The present disclosure relates to a class of donors containing both a carbamate and ester that functionally support polymerization catalysts showing an excellent balance of activity and stereospecificity.

Accordingly, the present disclosure provides for a catalyst component for the polymerization of olefins comprising Mg, Ti and an electron donor of the general formula (I):

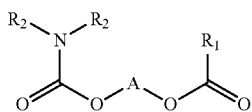
(I)

where $R_1$ is selected from $C_1$-$C_{15}$ hydrocarbon groups, optionally containing a heteroatom selected from halogen, P, S, N and O; $R_2$ groups, equal to or different from each other, may be hydrogen or $R_1$ groups which can be fused together to form one or more cycles, and A is a bivalent bridging group.

DETAILED DESCRIPTION OF THE INVENTION

In some embodiments, A is a bivalent bridging group with a chain length between the two bridging bonds of 1-10 atoms. In the case of cyclic structures that act as bridging groups, the term "chain length" refers to the shortest sequence of atoms bridging the oxygen atoms of formula (I). In one embodiment, the bridging group has formula —$(ZR^3_m)_n$— in which, independently, Z is selected from C, Si, Ge, O, N, S and P, the $R^3$ groups, equal to or different from each other, are hydrogen or a $C_1$-$C_{20}$ hydrocarbon radicals, optionally containing a heteroatom selected from halogen, P, S, N, O and Si, which can be fused together to form one or more cycles, m is a number satisfying the valences of Z, and n is an integer ranging from 1 to 10. In certain embodiments, the bridging group of the general formula —$(ZR^3_m)_n$— is utilized such that the atoms O, S, and N are not directly linked to the oxygen of formula (I), i.e. they are not the terminal atoms of the bridging group. In further embodiments, Z is selected from C and Si.

In a particular embodiment, the bivalent bridging group is selected from the group consisting of aliphatic, alicyclic and aromatic bivalent radicals, optionally substituted with $C_1$-$C_{15}$ hydrocarbon groups and/or with heteroatoms selected from halogen, P, S, N, O and Si, and having a bridging chain length ranging from 1 to 6 atoms, such as from 1 to 4 atoms.

In some embodiments, the bridging group is an aliphatic or alicyclic bridging group having a bridging chain length of 1-6 carbon atoms. Among this class, bridging groups may include those of the general formula —$(CR^4_p)_s$— in which $R^4$ is independently hydrogen or a $C_1$-$C_{20}$ hydrocarbon radicals, optionally substituted with heteroatoms selected from halogen, P, S, N, O and Si, which can be fused together to form one or more cycles, p is a number satisfying the available valence of carbon and s is a number from 1 to 6, such as from 1 to 4. Examples of bridging groups are methylidene, ethane-1,2-diyl, butane-2,3-diyl, pentane-2,4-diyl, 2,2-diisobutylpropane-1,3-diyl, cyclohexane-1,2-diyl and cyclopentane-1,2-diyl.

Another bridging group for use in the present technology is the one based on cyclic aromatic groups, which through the carbon ring atoms can link to the two oxygens of formula (I). Among them, phenyl groups, optionally substituted with halogens or $C_1$-$C_{20}$ alkyl radicals, may be used for bridging the oxygen atoms in position 1,2 or 1,3 or 1,4 and the naphthalene groups, optionally substituted bridging the oxygen groups in position 1,2 or 2,3 or 1,8. In certain embodiments, the bridging group has the general structure of formula (II) below:

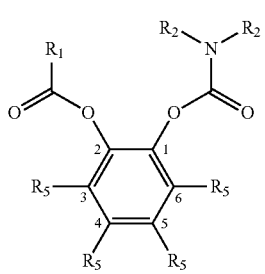

(II)

in which $R_1$ and $R_2$ have the same meaning previously specified, and $R_5$, independently, is selected from hydrogen, halogens and $C_1$-$C_{15}$ hydrocarbon groups optionally substituted with heteroatoms selected from halogen, P, S, N, O and Si, such that at least one of $R_5$ is different from hydrogen.

In certain embodiments, structures of formula (II) are those in which at least two of the $R_5$ groups are different from hydrogen. The aromatic ring of formula (II) is substituted in position 3, 4, 5 and/or 6. In all these cases, $R_5$ groups may be selected from $C_1$-$C_5$ alkyl groups. In some embodiments, substitution in position 3 and/or 6 with a primary alkyl group such as methyl, and in position 4 and/or 5 with a tertiary alkyl group such as tert-butyl, may be used.

Specific examples of aromatic bridging groups are 1,2-phenylene, 3-methyl-1,2-phenylene, 4-chloro-1,2-phenylene, 4-(tert-butyl)-1,2-phenylene, 3,6-dimethyl-1,2-phenylene, 3,5-dimethyl-1,2-phenylene, 5-(tert-butyl)-3-methyl-1,2-phenylene, 3,5-diisopropyl-1,2-phenylene, naphthalene-1,8-diyl, naphthalene-1,2-diyl and naphthalene-2,3-diyl groups.

In some embodiments, in the formulas (I) and (II) the $R_1$ groups are independently selected from $C_1$-$C_{15}$ alkyl groups, $C_6$-$C_{14}$ aryl groups, $C_3$-$C_{15}$ cycloalkyl groups, and $C_7$-$C_{15}$ arylalkyl or alkylaryl groups. The same applies to $R_2$ groups, which can additionally be hydrogen. In certain embodiments, the $R_1$ groups in formulae (I) and (II) are aryl or alkylaryl groups such as phenyl groups substituted with halogen and/or $C_1$-$C_5$ alkyl groups.

In further embodiments, in the formulas (I) and (II) the $R_2$ groups are independently selected from hydrogen or $C_1$-$C_{10}$ alkyl groups, including hydrogen or $C_1$-$C_5$ alkyl groups such as ethyl.

In some embodiments, the final amount of electron donor compound in the solid catalyst component ranges from 1 to 25% by weight, including from 3 to 20% by weight.

Non-limiting examples of structures of formulas (I) and (II) include 1-((diethylcarbamoyl)oxy)propan-2-yl 4-butylbenzoate, 1-((diethylcarbamoyl)oxy)propan-2-yl 4-chlorobenzoate, 1-((diethylcarbamoyl)oxy)propan-2-yl 4-ethylbenzoate, 1-((diethylcarbamoyl)oxy)propan-2-yl 4-methylbenzoate, 1-((diethylcarbamoyl)oxy)propan-2-yl 4-propylbenzoate, 1-((diethylcarbamoyl)oxy)propan-2-yl benzoate, 2-((diethylcarbamoyl)oxy)ethyl 4-butylbenzoate, 2-((diethylcarbamoyl)oxy)ethyl 4-chlorobenzoate, 2-((diethylcarbamoyl)oxy)ethyl 4-ethylbenzoate, 2-((diethylcarbamoyl)oxy)ethyl 4-methylbenzoate, 2-((diethylcarbamoyl)oxy)ethyl 4-propylbenzoate, 2-((diethylcarbamoyl)oxy)ethyl benzoate, 2-((diethylcarbamoyl)oxy)propyl 4-butylbenzoate, 2-((diethylcarbamoyl)oxy)propyl 4-chlorobenzoate, 2-((diethylcarbamoyl)oxy)propyl 4-ethylbenzoate, 2-((diethylcarbamoyl)oxy)propyl 4-methylbenzoate, 2-((diethylcarbamoyl)oxy)propyl 4-propylbenzoate, 2-((diethylcarbamoyl)oxy)propyl benzoate, 3-((diethylcarbamoyl)oxy)butan-2-yl 4-butylbenzoate, 3-((diethylcarbamoyl) oxy)butan-2-yl 4-chlorobenzoate, 3-((diethylcarbamoyl) oxy)butan-2-yl 4-ethylbenzoate, 3-((diethylcarbamoyl)oxy) butan-2-yl 4-methylbenzoate, 3-((diethylcarbamoyl)oxy) butan-2-yl 4-propylbenzoate, 3-((diethylcarbamoyl)oxy) butan-2-yl benzoate, 4-(carbamoyloxy)pentan-2-yl 4-butylbenzoate, 4-(carbamoyloxy)pentan-2-yl 4-chlorobenzoate, 4-(carbamoyloxy)pentan-2-yl 4-ethylbenzoate, 4-(carbamoyloxy)pentan-2-yl 4-methylbenzoate, 4-(carbamoyloxy)pentan-2-yl 4-propylbenzoate, 4-(carbamoyloxy)pentan-2-yl benzoate, 4-((dimethylcarbamoyl)oxy) pentan-2-yl 4-butylbenzoate, 4-((dimethylcarbamoyl)oxy) pentan-2-yl 4-chlorobenzoate, 4-((dimethylcarbamoyl)oxy) pentan-2-yl 4-ethylbenzoate, 4-((dimethylcarbamoyl)oxy) pentan-2-yl 4-methylbenzoate, 4-((dimethylcarbamoyl)oxy) pentan-2-yl 4-propylbenzoate, 4-((dimethylcarbamoyl)oxy) pentan-2-yl benzoate, 4-((diethylcarbamoyl)oxy)pentan-2-yl 4-butylbenzoate, 4-((diethylcarbamoyl)oxy)pentan-2-yl 4-chlorobenzoate, 4-((diethylcarbamoyl)oxy)pentan-2-yl 4-ethylbenzoate, 4-((diethylcarbamoyl)oxy)pentan-2-yl 4-methylbenzoate, 4-((diethylcarbamoyl)oxy)pentan-2-yl 4-propylbenzoate, 4-((diethylcarbamoyl)oxy)pentan-2-yl benzoate, 4-((diisopropylcarbamoyl)oxy)pentan-2-yl 4-butylbenzoate, 4-((diisopropylcarbamoyl)oxy)pentan-2-yl 4-chlorobenzoate, 4-((diisopropylcarbamoyl)oxy)pentan-2-yl 4-ethylbenzoate, 4-((diisopropylcarbamoyl)oxy)pentan-2-yl 4-methylbenzoate, 4-((diisopropylcarbamoyl)oxy)pentan-2-yl 4-propylbenzoate, 4-((diisopropylcarbamoyl)oxy) pentan-2-yl benzoate, 4-((diphenylcarbamoyl)oxy)pentan-2-yl 4-butylbenzoate, 4-((diphenylcarbamoyl)oxy)pentan-2-yl 4-chlorobenzoate, 4-((diphenylcarbamoyl)oxy)pentan-2-yl 4-ethylbenzoate, 4-((diphenylcarbamoyl)oxy)pentan-2-yl 4-methylbenzoate, 4-((diphenylcarbamoyl)oxy)pentan-2-yl 4-propylbenzoate, 4-((diphenylcarbamoyl)oxy)pentan-2-yl benzoate, 3-((diethylcarbamoyl)oxy)-2,2-dimethylpropyl 4-butylbenzoate, 3-((diethylcarbamoyl)oxy)-2,2-dimethylpropyl 4-chlorobenzoate, 3-((diethylcarbamoyl)oxy)-2,2-dimethylpropyl 4-propylbenzoate, 3-((diethylcarbamoyl) oxy)-2,2-dimethylpropylbenzoate, 2-(((diethylcarbamoyl) oxy)methyl)-2-isopropyl-3-methylbutyl 4-butylbenzoate, 2-(((diethylcarbamoyl)oxy)methyl)-2-isopropyl-3-methylbutyl 4-chlorobenzoate, 2-(((diethylcarbamoyl)oxy) methyl)-2-isopropyl-3-methylbutyl 4-propylbenzoate, 2-(((diethylcarbamoyl)oxy)methyl)-2-isopropyl-3-methylbutyl benzoate, (9-(((diethylcarbamoyl)oxy)methyl)-9H-fluoren-9-yl)methyl 4-butylbenzoate, (9-(((diethylcarbamoyl)oxy)methyl)-9H-fluoren-9-yl)methyl 4-chlorobenzoate, (9-(((diethylcarbamoyl)oxy)methyl)-9H-fluoren-9-yl) methyl 4-propylbenzoate, (9-(((diethylcarbamoyl)oxy) methyl)-9H-fluoren-9-yl)methyl benzoate, 2-((diethylcarbamoyl)oxy)cyclohexyl 4-butylbenzoate, 2-((diethylcarbamoyl)oxy)cyclohexyl 4-chlorobenzoate, 2-((diethylcarbamoyl)oxy)cyclohexyl 4-propylbenzoate, 2-((diethylcarbamoyl)oxy)cyclohexyl benzoate, 2-((diethylcarbamoyl)oxy)cyclopentyl 4-butylbenzoate, 2-((diethylcarbamoyl)oxy)cyclopentyl 4-chlorobenzoate, 2-((diethylcarbamoyl)oxy)cyclopentyl 4-propylbenzoate, 2-((diethylcarbamoyl)oxy)cyclopentyl benzoate, 4-(((diethylcarbamoyl)oxy)methyl)-3-isopropyl-5-methylhexyl 4-butylbenzoate, 4-(((diethylcarbamoyl)oxy)methyl)-3-isopropyl-5-methylhexyl 4-chlorobenzoate, 4-(((diethylcarbamoyl)oxy)methyl)-3-isopropyl-5-methylhexyl 4-propylbenzoate, 4-(((diethylcarbamoyl)oxy) methyl)-3-isopropyl-5-methylhexyl benzoate, 2-((diethylcarbamoyl)oxy)phenyl 4-butylbenzoate, 2-((diethylcarbamoyl)oxy)phenyl 4-chlorobenzoate, 2-((diethylcarbamoyl)oxy)phenyl 4-m ethylbenzoate, 2-((diethylcarbamoyl)oxy)phenyl benzoate, 4-(tert-butyl)-2-((diethylcarbamoyl)oxy)-6-methylphenyl 4-butylbenzoate, 4-(tert-butyl)-2-((diethylcarbamoyl)oxy)-6-methylphenyl 4-chlorobenzoate, 4-(tert-butyl)-2-((diethylcarbamoyl)oxy)-6-methyl phenyl 4-ethylbenzoate, 4-(tert-butyl)-2-((diethylcarbamoyl)oxy)-6-methylphenyl 4-methylbenzoate, 4-(tert-butyl)-2-((diethylcarbamoyl)oxy)-6-methylphenyl 4-propylbenzoate, 4-(tert-butyl)-2-((diethylcarbamoyl)oxy)-6-methylphenyl benzoate, 4-(tert-butyl)-2-((diethylcarbamoyl)oxy)phenyl 4-butylbenzoate, 4-(tert-butyl)-2-((diethylcarbamoyl)oxy)phenyl 4-chlorobenzoate, 4-(tert-butyl)-2-((diethylcarbamoyl)oxy)phenyl 4-ethylbenzoate, 4-(tert-butyl)-2-((diethylcarbamoyl)oxy)phenyl 4-methylbenzoate, 4-(tert-butyl)-2-((diethylcarbamoyl)oxy)phenyl 4-propylbenzoate, 4-(tert-butyl)-2-((diethylcarbamoyl)oxy)phenyl benzoate, 5-(tert-butyl)-2-((diethylcarbamoyl)oxy)-3-methylphenyl 4-butylbenzoate, 5-(tert-butyl)-2-((diethylcarbamoyl)oxy)-3-methylphenyl 4-chlorobenzoate, 5-(tert-butyl)-2-((diethylcarbamoyl)oxy)-3-methyl phenyl 4-ethylbenzoate, 5-(tert-butyl)-2-((diethylcarbamoyl)oxy)-3-methyl phenyl 4-m ethylbenzoate, 5-(tert-butyl)-2-((diethylcarbamoyl)oxy)-3-methylphenyl 4-propylbenzoate, 5-(tert-butyl)-2-((diethylcarbamoyl)oxy)-3-methylphenyl benzoate, 5-(tert-butyl)-2-((diethylcarbamoyl)oxy)phenyl 4-butylbenzoate, 5-(tert-butyl)-2-((diethylcarbamoyl)oxy) phenyl 4-chlorobenzoate, 5-(tert-butyl)-2-((diethylcarbamoyl)oxy)phenyl 4-ethylbenzoate, 5-(tert-butyl)-2-((diethylcarbamoyl)oxy)phenyl 4-methylbenzoate, 5-(tert-butyl)-2-((diethylcarbamoyl)oxy)phenyl 4-propylbenzoate, 5-(tert-butyl)-2-((diethylcarbamoyl)oxy)phenyl benzoate, 4-(tert-butyl)-2-((diethylcarbamoyl)oxy)-6-methyl phenyl 3-chlorobenzoate, 5-(tert-butyl)-2-((diethylcarbamoyl)oxy)-3-methyl phenyl 3-chlorobenzoate, 4-(tert-butyl)-2-((diisopropylcarbamoyl)oxy)-6-methyl phenyl 4-butylbenzoate, 4-(tert-butyl)-2-((diisopropylcarbamoyl)oxy)-6-methylphenyl 4-propylbenzoate, 4-(tert-butyl)-2-((diisopropylcarbamoyl)oxy)-6-methylphenyl benzoate, 4-(tert-butyl)-2-((dimethylcarbamoyl)oxy)-6-methylphenyl 4-butylbenzoate, 4-(tert-butyl)-2-((dimethylcarbamoyl)oxy)-6-methylphenyl 4-propylbenzoate, 4-(tert-butyl)-2-((dimethylcarbamoyl)oxy)-6-methylphenyl benzoate, 4-(tert-butyl)-2-((diphenylcarbamoyl)oxy)-6-methyl phenyl 4-butylbenzoate, 4-(tert-butyl)-2-((diphenylcarbamoyl)oxy)-6-methyl phenyl 4-propylbenzoate, 4-(tert-butyl)-2-((diphenylcarbamoyl)oxy)-6-methylphenyl benzoate, 4-(tert-butyl)-2-(carbamoyloxy)-6-methylphenyl 4-butylbenzoate, 4-(tert-butyl)-2-(carbamoyloxy)-6-methyl phenyl 4-propylbenzoate, 4-(tert-butyl)-2-(carbamoyloxy)-6-methylphenyl benzoate, 5-(tert-butyl)-2-((diisopropylcarbamoyl)oxy)-3-methyl phenyl 4-butylbenzoate, 5-(tert-butyl)-2-((diisopropylcarbamoyl)oxy)-3-methylphenyl 4-propylbenzoate, 5-(tert-butyl)-2-((diisopropylcarbamoyl)oxy)-3-methylphenyl benzoate, 5-(tert-butyl)-2-((dimethylcarbamoyl)oxy)-3-methylphenyl 4-butylbenzoate, 5-(tert-butyl)-2-((dimethylcarbamoyl)oxy)-3-methylphenyl 4-propylbenzoate, 5-(tert-butyl)-2-((dimethylcarbamoyl)oxy)-3-methylphenyl benzoate, 5-(tert-butyl)-2-((diphenylcarbamoyl)oxy)-3-methyl phenyl 4-butylbenzoate, 5-(tert-butyl)-2-((diphenylcarbamoyl)oxy)-3-methyl phenyl 4-propylbenzoate, 5-(tert-butyl)-2-((diphenylcarbamoyl)oxy)-3-methylphenyl benzoate, 5-(tert-butyl)-2-(carbamoyloxy)-3-methylphenyl 4-butylbenzoate, 5-(tert-butyl)-2-(carbamoyloxy)-3-methyl phenyl 4-propylbenzoate, 5-(tert-butyl)-2-(carbamoyloxy)-3-methylphenyl benzoate, 4-(tert-butyl)-2-((diethylcarbamoyl)oxy) phenyl 4-butylbenzoate, 4-(tert-butyl)-2-((diethylcarbamoyl)oxy)phenyl 4-propylbenzoate, 5-(tert-butyl)-2-((diethylcarbamoyl)oxy)phenyl 4-butylbenzoate, 5-(tert-butyl)-2-((diethylcarbamoyl)oxy)phenyl 4-propylbenzoate, 1-((diethylcarbamoyl)oxy)naphthalen-2-yl 4-propylbenzoate, 2-((diethylcarbamoyl)oxy)-3,4,6-triisopropylphenyl 4-propylbenzoate, 2-((diethylcarbamoyl)oxy)-3,5,6-triisopropylphenyl 4-propylbenzoate, 2-((diethylcarbamoyl)oxy)-3,5-diisopropylphenyl 4-propylbenzoate, 2-((diethylcarbamoyl)oxy)-3,6-dimethylphenyl 4-propylbenzoate, 2-((diethylcarbamoyl)oxy)-3-isopropyl-6-methylphenyl 4-propylbenzoate, 2-((diethylcarbamoyl)oxy)-3-methylphenyl 4-propylbenzoate, 2-((diethylcarbamoyl)oxy)-4,6-diisopropylphenyl 4-propylbenzoate, 2-((diethylcarbamoyl)oxy)-4-isopropyl-3,6-dimethylphenyl 4-propylbenzoate, 2-((diethyl carbamoyl)oxy)-4-methylphenyl 4-propylbenzoate, 2-((diethylcarbamoyl)oxy)-5-isopropyl-3,6-dimethylphenyl 4-propylbenzoate, 2-((diethylcarbamoyl)oxy)-5-methylphenyl 4-propylbenzoate, 2-((diethylcarbamoyl)oxy)-6-isopropyl-3-methylphenyl 4-propylbenzoate, 2-((diethylcarbamoyl)oxy)-6-methylphenyl 4-propylbenzoate, 3,6-di-tert-butyl-2-((di ethyl carbamoyl)oxy)phenyl 4-propylbenzoate, 3-((diethylcarbamoyl)oxy)naphthalen-2-yl 4-propylbenzoate, 3-(tert-butyl)-6-((diethylcarbamoyl)oxy)-2,5-dimethylphenyl 4-propylbenzoate, 4-(tert-butyl)-2-((diethylcarbamoyl)oxy)-3,6-dimethylphenyl 4-propylbenzoate, 8-((diethylcarbamoyl)oxy)naphthalen-1-yl 4-propylbenzoate 4-(tert-butyl)-2-((diethylcarbamoyl)oxy)phenyl 3-chlorobenzoate, 5-(tert-butyl)-2-((diethylcarbamoyl)oxy)phenyl 3-chlorobenzoate, 4-(tert-butyl)-2-((diethylcarbamoyl)oxy)-6-methyl phenyl benzoate, 5-(tert-butyl)-2-((diethylcarbamoyl)oxy)-3-methylphenyl benzoate.

The compounds of formulas (I) and (II) can be prepared by reacting an excess of a starting diol having the general formula HO-A-OH with a suitable acyl chloride, followed by removal of the unreacted diol by aqueous washings, distillation or chromatographic techniques. The monoester-monoalcohol is then reacted with a suitable carbamoyl chloride. Both steps are often carried out in presence of a base and their order of reaction can be inverted.

When unsubstituted or substituted catechols are used as starting diols to prepare the donors according to formula (II), the corresponding monophenol-monocarbamate derivative can be obtained by reacting the starting compounds with a diphenyl carbonate and a proper secondary amine. The intermediate is then reacted with a suitable acyl chloride. In such a reaction, depending on the type of substitution on the catechol ring, positional isomers can be generated by the formation of the carbamic group on one of the two available hydroxyl groups of the catechol. While the presence of two different isomers and their respective ratio can be detected, it has not been possible until now to assign the specific structure to each of the respective isomers which, in any case, are defined by formula (II). Therefore, in the examples reported below it has been indicated that the catechol based electron donors are prepared as a mixture of positional isomers.

In the solid catalyst component of the present disclosure the amount of Ti atoms in the solid catalyst component may be higher than 2.5% by weight, including higher than 3.0% by weight, with respect to the total weight of the catalyst component.

As explained above, the catalyst components of the technology comprise, in addition to the electron donors described herein, Ti, Mg and halogen. he catalyst components comprise a titanium compound having at least a Ti-halogen bond and the above mentioned electron donor compounds supported on a Mg halide compound. The magnesium halide is, in some embodiments, $MgCl_2$ in an active form as described, e.g. in U.S. Pat. Nos. 4,298,718 and 4,495,338. It is known from these patents that magnesium dihalides in active form and used as supports or co-supports in components of catalysts for the polymerization of olefins are characterized by X-ray spectra in which the most intense diffraction line assignable to the non-active halide is diminished in intensity and replaced by a halo whose maximum intensity is displaced towards lower angles relative to that of the more intense line.

Titanium compounds that may be used in the catalyst component of the present technology include $TiCl_4$ and $TiCl_3$. Ti-haloalcoholates of the general formula $Ti(OR)_{m-y}X_y$ can also be used, where m is the valence of titanium, y is a number between 1 and m−1, X is halogen and R is a hydrocarbon radical having from 1 to 10 carbon atoms.

The preparation of the solid catalyst component can be carried out according to several methods, including the reaction between magnesium alcoholates or chloroalcoholates (in particular chloroalcoholates prepared according to U.S. Pat. No. 4,220,554) and an excess of $TiCl_4$ in the presence of the electron donor compounds at a temperature of about 80 to 120° C.

In certain embodiments, the solid catalyst component can be prepared by reacting a titanium compound of the general formula $Ti(OR)_{m-y}X_y$, where m is the valence of titanium and y is a number between 1 and m, including $TiCl_4$, with magnesium chloride derived, in some embodiments, from an adduct of the general formula $MgCl_2 \cdot pROH$, where p is a number between 0.1 and 6, such as 2 to 3.5, and R is a hydrocarbon radical having 1-18 carbon atoms. The adduct can be prepared in spherical form by mixing alcohol and magnesium chloride in the presence of an inert hydrocarbon immiscible with the adduct, operating under stirring conditions at the melting temperature of the adduct (100-130° C.). The emulsion is quickly quenched, thereby causing the solidification of the adduct in the form of spherical particles. Examples of spherical adducts prepared according to this procedure are described in U.S. Pat. Nos. 4,399,054 and 4,469,648. The resulting adduct can be directly reacted with Ti compound or subjected to thermally controlled dealcoholation (80-130° C.) to obtain an adduct in which the number of moles of alcohol is generally lower than 3, such as between 0.1 and 2.5. The reaction with the Ti compound can be carried out by suspending the adduct (dealcoholated or non-dealcoholated) in cold $TiCl_4$ (generally at a temperature of 0° C. The mixture is then heated to 80-130° C. and kept at this temperature for 0.5-2 hours. The treatment with $TiCl_4$ can be carried out one or more times. The electron donor compound may be added during the treatment with $TiCl_4$. The preparation of catalyst components in spherical form are described, for example, in European Patent Applications EP-A-395083, EP-A-553805, EP-A-553806, EPA601525 and WIPO Int. App. WO 98/44001.

The solid catalyst components obtained according to the above method show a surface area (by B.E.T. method) generally between 20 and 500 $m^2/g$, including between 50 and 400 $m^2/g$, and a total porosity (by B.E.T. method) higher than 0.2 $cm^3/g$, such as between 0.2 and 0.6 $cm^3/g$. The porosity (Hg method) due to pores with radius up to 10.000 Å generally ranges from 0.3 to 1.5 $cm^3/g$, such as from 0.45 to 1 $cm^3/g$.

The solid catalyst component has an average particle size ranging from 5 to 120 μm, including from 10 to 100 μm.

In any of these preparation methods, the electron donor compounds can be added in their commercially available forms or obtained in situ by using the appropriate precursors for producing the electron donor(s).

In certain embodiments, the final amount of the electron donor compound of formula (I) is such that its molar ratio with respect to the Ti atoms is from 0.01 to 2, including from 0.05 to 1.5.

The solid catalyst components according to the present technology are, in some embodiments, converted into catalysts for the polymerization of olefins by reacting them with organoaluminum compounds according to known methods.

In particular, it is an object of the present technology a catalyst for the polymerization of olefins $CH_2$=CHR, in which R is hydrogen or a hydrocarbyl radical with 1-12 carbon atoms, comprising the product obtained by contacting:
(i) the solid catalyst component as disclosed above and
(ii) an alkylaluminum compound and optionally,
(iii) an external electron donor compound.

In some embodiments, the alkyl-Al compound (ii) is chosen among the trialkyl aluminum compounds such as for example triethylaluminum, triisobutylaluminum, tri-n-butylaluminum, tri-n-hexylaluminum and tri-n-octylaluminum. It is also possible to use alkylaluminum halides, alkylaluminum hydrides or alkylaluminum sesquichlorides, such as $AlEt_2Cl$ and $Al_2Et_3Cl_3$, possibly in mixture with the above cited trialkylaluminums.

In certain embodiments, external electron-donor compounds for use in the present technology include silicon compounds, ethers, esters, amines, heterocyclic compounds, 2,2,6,6-tetramethylpiperidine and ketones.

Another class of external donor compounds for use with the present technology is silicon compounds of the general formula $(R_7)_a(R_8)_bSi(OR_9)_c$, where a and b are integers from 0 to 2, c is an integer from 1 to 4 and the sum (a+b+c) is 4; $R_7$, $R_8$, and $R_9$, are radicals with 1-18 carbon atoms optionally containing heteroatoms. In certain embodiments, silicon compounds in which a is 1, b is 1, c is 2, at least one of $R_7$ and $R_8$ is selected from branched alkyl, cycloalkyl or aryl groups with 3-10 carbon atoms optionally containing heteroatoms and $R_9$ is a $C_1$-$C_{10}$ alkyl group, such as a methyl group, may be used. Examples of such silicon compounds are methylcyclohexyldimethoxysilane (C donor), diphenyldimethoxysilane, methyl-t-butyldimethoxysilane, dicyclopentyldimethoxysilane (D donor), diisopropyldimethoxysilane, (2-ethylpiperidinyl)t-butyldimethoxysilane, (2-ethylpiperidinyl)thexyldimethoxysilane, (3,3,3-trifluoro-n-propyl)(2-ethylpiperidinyl)dimethoxysilane, methyl (3,3,3-trifluoro-n-propyl)dimethoxysilane and N,N-diethylaminotriethoxysilane. Additional external donor compounds for use in the present technology include silicon compounds in which a is 0, c is 3, $R_8$ is a branched alkyl or cycloalkyl group, optionally containing heteroatoms, and $R_9$ is methyl. Examples of such silicon compounds are cyclohexyltrimethoxysilane, t-butyltrimethoxysilane and thexyltrimethoxysilane.

In certain embodiments, the electron donor compound (iii) is used in such an amount to give a molar ratio between the organoaluminum compound and the electron donor compound (iii) of from 0.1 to 500, including from 1 to 300 and from 3 to 100.

Therefore, a further object of the present technology includes a process for the (co)polymerization of olefins $CH_2$=CHR, in which R is hydrogen or a hydrocarbyl radical with 1-12 carbon atoms, carried out in the presence of a catalyst comprising the product of the reaction between:
(i) the solid catalyst component of the present disclosure;
(ii) an alkylaluminum compound and,
(iii) optionally an electron-donor compound (external donor).

The polymerization process can be carried out according to known techniques, for example slurry polymerization using an inert hydrocarbon solvent as a diluent, or bulk polymerization using the liquid monomer (for example, propylene) as a reaction medium. Moreover, it is possible to carry out the polymerization process in gas-phase operating in one or more fluidized or mechanically agitated bed reactors.

The polymerization is generally carried out at temperature of from 20 to 120° C., including from 40 to 80° C. When the polymerization is carried out in gas-phase, the operating pressure is generally between 0.5 and 5 MPa, such as between 1 and 4 MPa. In bulk polymerization processes, the operating pressure may be between 1 and 8 MPa, including between 1.5 and 5 MPa.

The following examples are given in order to further illustrate non-limiting embodiments of the present technology.

Characterizations

Determination of X.I.

2.5 g of polymer and 250 ml of o-xylene were placed in a round-bottomed flask operably connected to a cooler and a reflux condenser and kept under nitrogen. The resulting mixture was heated to 135° C. and was kept under stirring for about 60 minutes. The final solution was allowed to cool to 25° C. under continuous stirring, and the insoluble polymer was then filtered. The filtrate was then evaporated in a nitrogen flow at 140° C. to reach a constant weight. The content of the xylene-soluble fraction is expressed as a percentage of the original 2.5 grams and then, by difference, the xylene insolubility percentage (X.I. %).

Determination of Electron Donors.

The electron donor analysis was carried out via gas-chromatography. The solid component was dissolved in acidic water. The solution was extracted with ethyl acetate, an internal standard was added and a sample of the organic phase was analyzed in a gas chromatograph, to determine the amount of donor present at the starting catalyst compound.

Melt Flow Rate (MFR)

The melt flow rate MIL of the polymer was determined according to ISO 1133 (230° C., 2.16 kg).

EXAMPLES

Example 1

Synthesis of 4-((diethylcarbamoyl)oxy)pentan-2-yl 4-propylbenzoate

First Step: Synthesis of 4-hydroxypentan-2-yl 4-propylbenzoate

A 1000 mL reaction vessel was charged with 2,4-pentanediol (25 g, 237.8 mmol), triethylamine (31.6 g, 1.3 eq), 4-(dimethylamino)pyridine (0.29 g, 0.01 eq) and THF (600 mL). The mixture was cooled to −5° C. and 4-propylbenzoyl chloride (43.5 g, 0.995 eq) was slowly added. The mixture was allowed to stir at ambient temperature for 6 hours (h). The resulting suspension was filtered and the white precipitate was washed 2 times with THF (100 mL in total). The resulting organic phase was concentrated on a rotary evaporator which resulted in a light yellow oil, which was purified by means of chromatography ($SiO_2$)—cyclohexane/ethyl acetate: 10/1 to 2/1. Yield: 42.8 g (71.9%)—light yellow oil—Syn/Anti=1/1. GC/MS: m/z=250.

Second Step: Synthesis of 4-((diethylcarbamoyl)oxy)pentan-2-yl 4-propylbenzoate

A 1000 mL reaction vessel was charged with 4-hydroxypentan-2-yl 4-propylbenzoate (42.8 g, 169.4 mmol), and pyridine (400 mL). Diethylcarbamoyl chloride (34.8 g, 1.5 eq) was slowly added and stirred under reflux for 46 h. Pyridine was concentrated and the resulting oil was diluted with ethyl acetate (100 mL). The resulting solution was washed with a saturated aqueous $NH_4Cl$ solution and a saturated aqueous NaCl solution. The organic phase was dried over $MgSO_4$, filtered and concentrated on a rotary evaporator which resulted in the crude product as oil. It was purified by means of chromatography ($SiO_2$)—Cyclohexane/ethyl acetate: 8/1. Yield: 44.8 g (75.7%)—light yellow oil—Syn/Anti=1/1. GC/MS: m/z=349.

Example 2

Synthesis of 4-((diethylcarbamoyl)oxy)pentan-2-yl benzoate

First Step: Synthesis of 4-hydroxypentan-2-yl diethylcarbamate

A 250 mL reaction vessel was charged with 4-((diethylcarbamoyl)oxy)pentan-2-yl 4-propylbenzoate (12.5 g, 35.4 mmol) and toluene (125 mL). Sodium methoxide (5.8 g, 3 eq) was slowly added at ambient temperature. The mixture was stirred at 60° C. for 12 h. The resulting suspension was filtered and the white precipitate was washed 2 times with toluene (60 mL in total). The organic phase was dried over $MgSO_4$, filtered and concentrated on a rotary evaporator which resulted in the production of an oil as the crude product. It was purified by means of chromatography ($SiO_2$)—cyclohexane/ethyl acetate: 6/1. Yield: 5.8 g (79.8%)—light yellow oil—Syn/Anti=1/1. GC/MS: m/z=203.

Second Step: Synthesis of 4-((diethylcarbamoyl)oxy)pentan-2-yl benzoate

A 250 mL reaction vessel was charged with benzoyl chloride (2.5 g, 21.3 mmol), pyridine (5 mL, 3 eq), THF (100 mL) and 4-hydroxypentan-2-yl diethylcarbamate (4.3 g, 21.3 mmol). The mixture was allowed to stir at 60° C. for 2 h. Then the mixture was quenched with diluted hydrochloric acid (HCl) and ethyl acetate and the organic layer was washed with water until a neutral pH was reached. The organic phase was anhydrified, filtered and concentrated on a rotary evaporator which resulted in the pure product. Yield: 6 g (84%)—light yellow oil—Syn/Anti=1/1. GC/MS: m/z=307.

Example 3

Synthesis of 4-((diethylcarbamoyl)oxy)pentan-2-yl 4-ethylbenzoate

The synthesis of 4-((diethylcarbamoyl)oxy)pentan-2-yl 4-ethylbenzoate is the same as the synthesis described in Example 2 second step, except that 4-ethylbenzoyl chloride is used instead of benzoyl chloride.

Example 4

Synthesis of 4-((diethylcarbamoyl)oxy)pentan-2-yl 4-butylbenzoate

The synthesis of 4-((diethylcarbamoyl)oxy)pentan-2-yl 4-butylbenzoate is the same as that of Example 2 second step, except that 4-butylbenzoyl chloride is used instead of benzoyl chloride

Example 5

Synthesis of a mixture of 4-(tert-butyl)-2-((diethylcarbamoyl)oxy)phenyl 3-chlorobenzoate and 5-(tert-butyl)-2-((diethylcarbamoyl)oxy)phenyl 3-chlorobenzoate First Step: Synthesis of a Mixture of 4-(tert-butyl)-2-hydroxyphenyl diethylcarbamate and 5-(tert-butyl)-2-hydroxyphenyl diethylcarbamate 50 g of 4-t-butylcatechol (300 mmol) are charged in a round bottom flask with THF (300 mL) and 65.5 g of diphenyl carbonate (306 mmol) under nitrogen at room temperature. Then 33 mL of diethylamine (315 mmol) are added slowly and dropwise and the mixture is stirred at room temperature until GC analysis shows the complete conversion of the starting catechol. Then the mixture is diluted with acidic water, extracted with diethyl ether, and the organic layer washed with water until a neutral pH is reached. The solvent is removed via rotavapor and the obtained oil is dissolved into i-hexane (500 mL) and washed several times with water until GC analysis shows the absence of phenol. The solvent is distilled away to afford a mixture of 4-(tert-butyl)-2-hydroxyphenyl diethylcarbamate and 5-(tert-butyl)-2-hydroxyphenyl diethylcarbamate that is used in the next steps without purification.

Second Step: Synthesis of a Mixture of 4-(tert-butyl)-2((diethylcarbamoyl)oxy)phenyl 3-chlorobenzoate and 5-(tert-butyl)-2-((diethylcarbamoyl)oxy) phenyl 3-chlorobenzoate 4.65 g of a mixture of 4-(tert-butyl)-2-hydroxyphenyl diethylcarbamate and 5-(tert-butyl)-2-hydroxyphenyl diethylcarbamate (17.5 mmol), prepared in the previous step, is charged in a round bottom flask with THF (20 mL) and 2.7 mL of $Et_3N$ (19.3 mmol) under nitrogen at room temperature. Then 2.3 mL of 3-chlorobenzoyl chloride (17.9 mmol) are added carefully and dropwise. After 1.5 hours, acidic water is added and the mixture is extracted with diethyl ether. The organic layer is washed with water until a neutral pH is reached, then the organic layer is anhydrified over $Na_2SO_4$ and the solvent is distilled off, resulting in 7 g of product (99% of yield) with a GC purity of 99%.

Example 6

Synthesis of a Mixture of 4-(tert-butyl)-2-((diethylcarbamoyl)oxy)phenyl 4-chlorobenzoate and 5-(tert-butyl)-2-((diethylcarbamoyl)oxy)phenyl 4-chlorobenzoate The synthesis is the same as in Example 5 except that in the second step 4-chlorobenzoyl chloride is used instead of 3-chlorobenzoyl chloride.

Example 7

Synthesis of a Mixture of 4-(tert-butyl)-2-((diethylcarbamoyl)oxy)-6-methylphenyl 3-chlorobenzoate and 5-(tert-butyl)-2-((diethylcarbamoyl)oxy)-3-methylphenyl 3-chlorobenzoate The synthesis is the same as that of Example 5 except that 5-(tert-butyl)-3-methylcatechol is used in the first step instead of 4-t-butylcatechol.

Example 8

Synthesis of a Mixture of 4-(tert-butyl)-2-((diethylcarbamoyl)oxy)-6-methylphenyl 4-chlorobenzoate and 5-(tert-butyl)-2-((diethylcarbamoyl)oxy)-3-methylphenyl 4-chlorobenzoate The synthesis is the same as that of Example 7 except that 4-chlorobenzoyl chloride is used in the second step instead of 3-chlorobenzoyl chloride.

Example 9

Synthesis of a Mixture of 4-(tert-butyl)-2-((diethylcarbamoyl)oxy)-6-methylphenyl benzoate and 5-(tert-butyl)-2-((diethylcarbamoyl)oxy)-3-methylphenyl benzoate The synthesis is the same as that of Example 7 except that benzoyl chloride is used in the second step instead of 3-chlorobenzoyl chloride.

N-Z-L-proline methyl ester (Sigma Aldrich, St. Louis, Mo., USA) was used in Comparative Example 1.

General Procedure for the Preparation of the Spherical Adducts

An initial amount of microspheroidal $MgCl_2.8C_2H_5OH$ was prepared according to the method described in Example 2 of WO 98/44009, but carried out on a larger scale.

General Procedure for the Preparation of the Solid Catalyst Component

Into a 500 mL round bottom flask, equipped with mechanical stirrer, cooler and thermometer, 250 mL of $TiCl_4$ were introduced at room temperature under nitrogen atmosphere. After cooling to 0° C., while stirring, the internal donor and 10.0 g of the spherical adduct (prepared as described above) were sequentially added into the flask. The amount of charged internal donor was such to charge a Mg/donor molar ratio of 6. The temperature was raised to 100° C. and maintained for 2 hours. Thereafter, stirring was stopped, the solid product was allowed to settle and the supernatant liquid was siphoned off at 100° C. After the supernatant was removed, additional $TiCl_4$ was added to reach the initial liquid volume again. The mixture was then heated at 120° C. and kept at this temperature for 1 hour. Stirring was stopped again, the solid was allowed to settle and the supernatant liquid was siphoned off.

The solid was washed with anhydrous hexane six times (6×100 mL) using a temperature gradient down to 60° C. and one time (100 mL) at room temperature. The resulting solid was then dried under vacuum and analyzed.

General Procedure for the Polymerization of Propylene

A 4-liter steel autoclave equipped with a stirrer, pressure gauge, thermometer, catalyst feeding system, monomer feeding lines and thermostatic jacket, was purged with nitrogen flow at 70° C. for one hour. Then, at 30° C. under propylene flow, the reaction contents were charged in sequence with 75 mL of anhydrous hexane, 0.76 g of AlEt₃, the external electron donor indicated in Table 1 (if used) and 0.006-0.010 g of solid catalyst component. The autoclave was closed; subsequently 2.0 nL of hydrogen were added. Then, under stirring, 1.2 kg of liquid propylene was fed. The temperature was raised to 70° C. in five minutes and the polymerization was carried out at this temperature for two hours. At the end of the polymerization, the non-reacted propylene was removed; the polymer was recovered and dried at 70° C. under vacuum for three hours. Then the polymer was weighed and fractionated with o-xylene to determine the amount of the xylene insoluble (X.I.) fraction.

Examples 1-9 and Comparative Example 1

The catalyst components were prepared according to the general procedure using the donors indicated in Table 1. The resulting solid catalyst components were analyzed and tested for their ability to catalyze the polymerization of propylene using the procedure described above. The results are listed in Table 1.

TABLE 1

| | Catalyst composition | | | | Polymerization | | |
|---|---|---|---|---|---|---|---|
| | Internal Donor | | Ti | | Mileage | XI | MIL |
| | Name | % wt | % wt | ED | kg/g | % wt | g/10' |
| 1 | 4-((diethylcarbamoyl)oxy)pentan-2-yl 4-propylbenzoate | 9.1 | 4.0 | D | 74 | 98.3 | 1.7 |
| 2 | 4-((diethylcarbamoyl)oxy)pentan-2-yl benzoate | 8.1 | 4.3 | D | 59 | 97.5 | 1.2 |
| 3 | 4-((diethylcarbamoyl)oxy)pentan-2-yl 4-ethylbenzoate | 8.8 | 4.2 | D | 61 | 98.4 | 0.5 |
| 4 | 4-((diethylcarbamoyl)oxy)pentan-2-yl 4-butylbenzoate | 12.9 | 4.3 | D | 75 | 98.7 | 0.4 |

TABLE 1-continued
| | Catalyst composition | | | Polymerization | | |
|---|---|---|---|---|---|---|
| | Internal Donor | | Ti | Mileage | XI | MIL |
| | Name | % wt | % wt | ED | kg/g | % wt | g/10' |
| 5 | | | 17.1 | 4.9 | D | 73 | 98.0 | 0.6 |
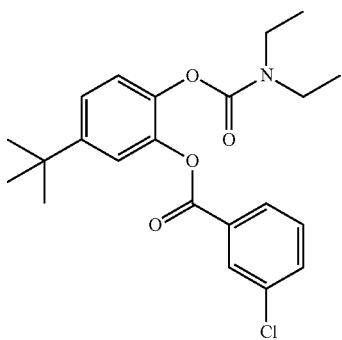 [SMILES: CCN(CC)C(=O)Oc1ccc(C(C)(C)C)cc1OC(=O)c1cccc(Cl)c1]
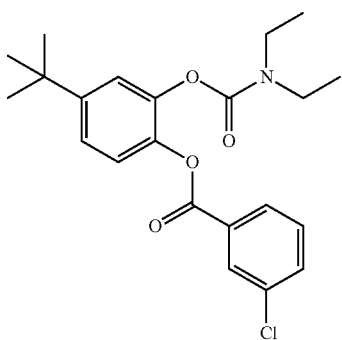 [SMILES: CCN(CC)C(=O)Oc1cc(C(C)(C)C)ccc1OC(=O)c1cccc(Cl)c1]
4-(tert-butyl)-2-
((diethylcarbamoyl)oxy)
phenyl 3-chlorobenzoate and
5-(tert-butyl)-2-
((diethylcarbamoyl)oxy)ph
enyl 3-chlorobenzoate
| 6 | | 8.1 | 4.1 | D | 64 | 97.5 | 0.2 |
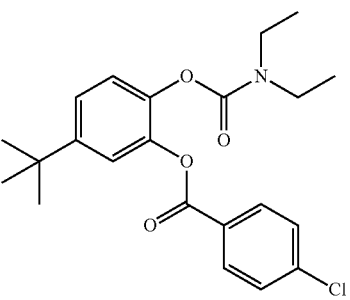 [SMILES: CCN(CC)C(=O)Oc1ccc(C(C)(C)C)cc1OC(=O)c1ccc(Cl)cc1]

TABLE 1-continued

| Catalyst composition | | | Polymerization | | |
|---|---|---|---|---|---|
| Internal Donor | | Ti | Mileage | XI | MIL |
| Name | % wt | % wt ED | kg/g | % wt | g/10' |

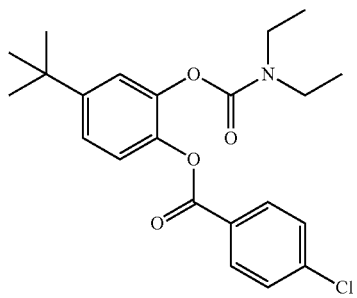 [SMILES: CCN(CC)C(=O)Oc1cc(C(C)(C)C)ccc1OC(=O)c1ccc(Cl)cc1]

4-(tert-butyl)-2-
((diethylcarbamoyl)oxy)(phenyl
4-chlorobenzoate and 5-(tert-
butyl)-2-
((diethylcarbamoyl)oxy)phenyl
4-chlorobenzoate 7      14.6   4.7   D   65   98.6   0.4

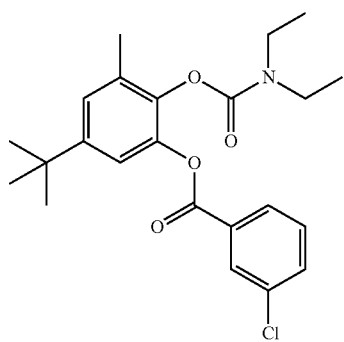 [SMILES: CCN(CC)C(=O)Oc1c(C)cc(C(C)(C)C)cc1OC(=O)c1cccc(Cl)c1]

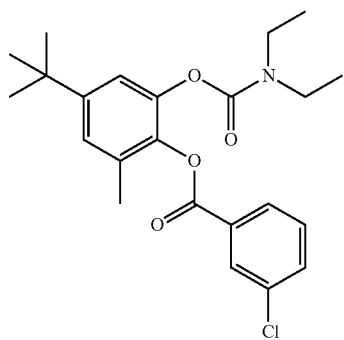 [SMILES: CCN(CC)C(=O)Oc1cc(C(C)(C)C)cc(C)c1OC(=O)c1cccc(Cl)c1]

4-(tert-butyl)-2-
((diethylcarbamoyl)oxy)-6-
methylphenyl 3-chlorobenzoate
and 5-(tert-butyl)-2-
((diethylcarbamoyl)oxy)-3-
methylphenyl 3-chlorobenzoate TABLE 1-continued

| | Catalyst composition | | | | Polymerization | | |
|---|---|---|---|---|---|---|---|
| | Internal Donor | | Ti | | Mileage | XI | MIL |
| | Name | % wt | % wt | ED | kg/g | % wt | g/10' |
| 8 | 4-(tert-butyl)-2-((diethylcarbamoyl)oxy)-6-methylphenyl 4-chlorobenzoate and 5-(tert-butyl)-2-((diethylcarbamoyl)oxy)-3-methylphenyl 4-chlorobenzoate | 17.3 | 4.6 | D | 98 | 97.7 | 0.3 |
| 9 | 4-(tert-butyl)-2-((diethylcarbamoyl)oxy)-6-methylphenyl benzoate and 5-(tert-butyl)-2-((diethylcarbamoyl)oxy)-3-methylphenyl benzoate | n.d. | 4.8 | D | 65 | 96.3 | 0.6 |

TABLE 1-continued

| Catalyst composition | | | | Polymerization | | |
|---|---|---|---|---|---|---|
| Internal Donor | | Ti | | Mileage | XI | MIL |
| Name | % wt | % wt | ED | kg/g | % wt | g/10' |
| C 1 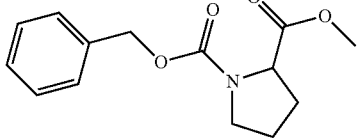<br>N-L-Z-Proline methyl ester | n.d. | 5.4 | D | 13 | 93.1 | 6.9 |

ED: External Donor.
D: dicyclopeniyldimethoxysilane
nd: not determined

What is claimed is:

1. A solid catalyst component for the polymerization of olefins comprising Mg, Ti and an electron donor of formula (I)

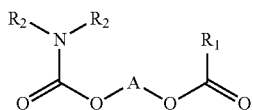

where $R_1$ is selected from $C_1$-$C_{15}$ hydrocarbon groups, optionally containing a heteroatom selected from halogen, P, S, N and O; $R_2$ groups, equal to or different from each other, are hydrogen or $R_1$ groups which can be fused together to form one or more cycles and A is a bivalent bridging group.

2. The catalyst component of claim 1, in which A is bivalent bridging group with chain length between the two free radicals being 1-10 atoms.

3. The catalyst component of claim 1, in which the bridging group has formula $-(ZR^3{}_m)_n-$ in which, independently, Z is selected from C, Si, Ge, O, N, S or P, the $R^3$ groups, equal to or different from each other, are hydrogen or $C_1$-$C_{20}$ hydrocarbon radicals, optionally containing a heteroatom selected from halogen, P, S, N, O and Si, which can be fused together to form one or more cycles, m is a number satisfying the valences of Z and n is an integer ranging from 1 to 10.

4. The catalyst component of claim 3, in which the bridging group is an aliphatic or alicyclic bridging group having a bridging chain length of 1-6 carbon atoms.

5. The catalyst component of claim 4, in which the bridging group has formula $-(CR^4{}_p)_s-$ in which $R^4$ is, independently, hydrogen or a $C_1$-$C_{20}$ hydrocarbon radical, optionally substituted with heteroatoms selected from halogen, P, S, N, O and Si, which can be fused together to form one or more cycles, p is a number satisfying the available valence of carbon and s is a number from 1 to 6.

6. The catalyst component of claim 5, in which the bridging group is selected from the group consisting of methyliden, ethane-1,2-diyl, butane-2,3-diyl, pentane-2,4-diyl, 2,2-diisobutylpropane-1,3-diyl, cyclohexane-1,2-diyl, and cyclopentane -1,2-diyl.

7. The catalyst component of claim 1, in the which $R_1$ groups are selected from aryl and alkylaryl groups.

8. The catalyst component of claim 7, in which $R_1$ groups are selected from phenyl groups.

9. The catalyst component of claim 8, in which the phenyl groups are substituted with halogen and/or $C_1$-$C_5$ alkyl groups.

10. The catalyst component of claim 1, in which $R_2$ groups are independently selected from hydrogen or $C_1$-$C_{10}$ alkyl groups.

11. The catalyst component of claim 3, in which the bridging group is the one based on cyclic aromatic groups which through the carbon ring atoms can link the two oxygen of formula (I).

12. The catalyst component of claim 11, in which the electron donor is selected from those having the following formula (II):

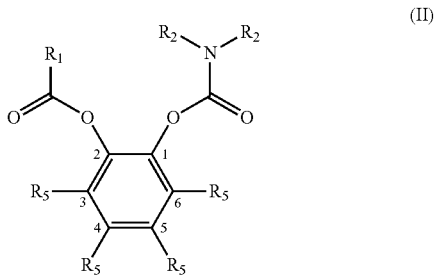

in which $R_1$ and $R_2$ have the same meaning according to claim 1, and $R_5$, independently, is selected from hydrogen, halogens or $C_1$-$C_{15}$ hydrocarbon groups optionally substituted with heteroatoms selected from halogen, P, S, N, O and Si, with the proviso that at least one of $R_5$ is different from hydrogen.

13. A catalyst for the polymerization of olefins comprising the product of the reaction between:
   (i) the solid catalyst component according to any of the preceding claims and
   (ii) an alkylaluminum compound and optionally,
   (iii) an external electron donor compound.

14. The catalyst of claim 13, further comprising an external electron donor compound.

15. A process for the (co)polymerization of olefins $CH_2=CHR$, in which R is hydrogen or a hydrocarbyl radical with 1-12 carbon atoms, carried out in the presence of a catalyst system comprising the product of the reaction between:
   i. the solid catalyst component of claim 1;
   ii. an alkylaluminum compound and,
   iii. optionally an external donor compound.

* * * * *